US012110485B2

(12) United States Patent
Liao et al.

(10) Patent No.: US 12,110,485 B2
(45) Date of Patent: Oct. 8, 2024

(54) LEUCONOSTOC CITREUM AND USE THEREOF IN PRECIPITATING STARCH EMULSION

(71) Applicants: CHINA AGRICULTURAL UNIVERSITY, Beijing (CN); SISHUI LIFENG FOOD CO., LTD., Jining (CN)

(72) Inventors: Xiaojun Liao, Beijing (CN); Xuan Wang, Beijing (CN); Liang Zhao, Beijing (CN); Yongtao Wang, Beijing (CN); Xiankui Kong, Beijing (CN); Hongyan Chen, Beijing (CN); Xueqiang Wang, Beijing (CN); Guanghua Li, Beijing (CN)

(73) Assignees: CHINA AGRICULTURAL UNIVERSITY, Beijing (CN); SISHUI LIFENG FOOD CO., LTD., Shandong (CN)

( * ) Notice: Subject to any disclaimer, the term of this patent is extended or adjusted under 35 U.S.C. 154(b) by 372 days.

(21) Appl. No.: 17/312,013

(22) PCT Filed: Nov. 24, 2020

(86) PCT No.: PCT/CN2020/131077
§ 371 (c)(1),
(2) Date: Jun. 9, 2021

(87) PCT Pub. No.: WO2021/218130
PCT Pub. Date: Nov. 4, 2021

(65) Prior Publication Data
US 2023/0250389 A1    Aug. 10, 2023

(30) Foreign Application Priority Data
Apr. 29, 2020 (CN) .......................... 202010353037.8

(51) Int. Cl.
*C12N 1/20* (2006.01)
*C08B 30/04* (2006.01)
*C12P 19/04* (2006.01)
*C12R 1/01* (2006.01)

(52) U.S. Cl.
CPC ................ *C12N 1/20* (2013.01); *C08B 30/04* (2013.01); *C12N 1/205* (2021.05); *C12P 19/04* (2013.01); *C12R 2001/01* (2021.05)

(58) Field of Classification Search
CPC .......... C12N 1/20; C12N 1/205; C08B 30/04; C12P 19/04; C12R 2001/01
See application file for complete search history.

(56) References Cited

FOREIGN PATENT DOCUMENTS

| | | | |
|---|---|---|---|
| CN | 102492644 A | 6/2012 | |
| CN | 102625828 A | 8/2012 | |
| CN | 108034612 A | 5/2018 | |
| CN | 108285878 A | 7/2018 | |
| CN | 110804575 A | 2/2020 | |
| CN | 111154666 A | 5/2020 | |
| CN | 111254102 A | 6/2020 | |
| KR | 100560161 B1 | 3/2006 | |
| WO | 2011007924 A1 | 1/2011 | |
| WO | WO-2020094055 A1 * | 5/2020 | ............. A23L 29/30 |

OTHER PUBLICATIONS

Dellaglio et al., "The Genus *Leuconostoc*," in the Genera of Lactic Acid Bacteria, vol. 2, editors B.J.B. Wood, and W.H. Holzapfel (Boston, MA: Springer), 1995, p. 235-278. doi: 10.1007/978-1-4615-5817-0_7 (Year: 1995).*

\* cited by examiner

*Primary Examiner* — Aaron J Kosar
*Assistant Examiner* — Andrew T Moehlman (57) ABSTRACT

Provided is a method for precipitating a starch emulsion, the method including: mixing a fermentation broth with the starch emulsion, the fermentation broth including an isolated microorganism, wherein the isolated microorganism is *Leuconostoc citreum* WSJ-57 deposited under an accession number of CGMCC No. 19201 in the China General Microbiological Culture Collection Center on Dec. 20, 2019.

2 Claims, 5 Drawing Sheets

Specification includes a Sequence Listing.

ID Details:
- ID Called At: 22 Hours
- ID Status: Final ID
- Biolog ID-Database: GEN_III_v2.8.0.15G

| | |
|---|---|
| ID Result | Species ID: Leuconostoc citreum |
| ID Comment | |
| ID Notice | |

| Rank | PROB | SIM | DIST | Organism Type | Species |
|---|---|---|---|---|---|
| 1 | 0.907 | 0.873 | 1.741 | GP-Coccus | Leuconostoc citreum |
| 2 | 0.053 | 0.057 | 2.258 | GP-Rod-SB | Sporolactobacillus terrae |
| 3 | 0.021 | 0.036 | 2.674 | GP-Coccus | Lactococcus lactis ss hordniae |
| 4 | 0.019 | 0.034 | 2.708 | GP-Coccus | Leuconostoc mesenteroides ss dextranicum |

Key: <x: positive, x: negative, <x-: mismatched positive, x+: mismatched negative {x: borderline, -x: less than A1 well OmniLog Values

| Data | 1 | 2 | 3 | 4 | 5 | 6 | 7 | 8 | 9 | 10 | 11 | 12 |
|---|---|---|---|---|---|---|---|---|---|---|---|---|
| A | 20 | 25 | < 128 | < 178 | 11 | 11 | < 158 | < 138 | 11 | { 63 | 48 | 45 |
| B | 22 | 13 | 13 | 11 | < 72 | < 172 | 11 | 11 | 11 | 54 | 44 | 35 |
| C | < 115 | < 104 | < 163 | 15 | 11 | 14 | 19 | 16 | 11 | 39 | 46 | 49 |
| D | 18 | < 66 | 18 | 11 | 11 | 11 | 25 | 11 | 11 | 23 | 45 | 43 |
| E | 20 | 14 | 11 | 11 | 11 | 11 | 11 | 11 | 11 | 35 | 33 | 36 |
| F | < 63 | 25 | 17 | 34 | 38 | 46 | 12 | 11 | 13 | 57 | < 98 - | < 97 - |
| G | 19 | 18 | 14 | 13 | 18 | 13 | 14 | 11 | 12 | 57 | 34 | 73 |
| H | 29 | 23 | 18 | 21 | 21 | 22 | 25 | 34 | 21 | 60 | 47 | 42 |

Report Date | Nov 29 2019 8:08 AM          Version 2.4

LEUCONOSTOC CITREUM AND USE THEREOF IN PRECIPITATING STARCH EMULSION

REFERENCE TO SEQUENCE LISTING

This application contains a sequence listing submitted as an ASCII text file, named "Sequence-listing.txt" and created on Sep. 6, 2022, with 2.7 kilobytes in size. The material in the above-identified ASCII text file is incorporated herein by reference in its entirety.

TECHNICAL FIELD

The present disclosure relates to the biological field. In particular, the present disclosure relates to *Leuconostoc citreum* and use thereof in precipitating a starch emulsion.

BACKGROUND

Currently, sweet potato starch are produced with two production methods, namely, the sour liquid process and the centrifugal cyclone separator process. The vermicelli made of the sweet potato starch obtained by the sour liquor process has a better quality. The production of the sweet potato starch with the sour liquor process is a production method invented by the Chinese laboring people during the long-term production practice. A sour liquor is a slightly acidic and milky white liquid formed by natural fermentation of starch emulsion. The sour liquor is mainly used in the sedimentation process of sweet potato starch production. The sour liquor can be added to accelerate the sedimentation of starch, so as to separate the starch from protein, thereby improving starch purity. However, the production of starch with the traditional sour liquor process greatly depends on personal experience, and thus it is often affected by conditions such as the type and quantity of microorganism in the air, the temperature of the processing place, the metal components in the production water, the bacterial composition on the peel of sweet potato, the acidity of the sour liquor and other man-made factors. Therefore, the sour liquor has extremely unstable quality, which may affect the production efficiency and product quality of the starch to a certain extent.

In view of the above, it is still required to develop suitable microorganisms for starch sedimentation.

SUMMARY

The present disclosure aims to solve at least one of the technical problems existing in the prior art at least to a certain extent. The present disclosure provides a *Leuconostoc citreum* for efficiently flocculating and precipitating starch, which allows the starch to be rapidly and sufficiently precipitated, thereby improving the production efficiency of starch and having good application prospect.

To this end, in an aspect of the present disclosure, the present disclosure provides a microorganism. According to embodiments of the present disclosure, the microorganism is *Leuconostoc citreum* WSJ-57, which was deposited under an accession number of CGMCC No. 19201 in the China General Microbiological Culture Collection Center (CGMCC) on Dec. 20, 2019 (No. 3, Courtyard 1, Beichen West Road, Chaoyang District, Beijing). Applicant found that said *Leuconostoc citreum* has good flocculation rate and starch yield for the starch emulsion, and can precipitate the starch quickly and sufficiently, thereby improving the production efficiency of the starch and having a good application prospect.

In another aspect of the present disclosure, the present disclosure provides a fermentation broth. According to the embodiments of the present disclosure, the fermentation broth contains the aforementioned microorganism. As mentioned above, the microorganism according to the embodiments of the present disclosure has good flocculation rate and starch yield for the starch emulsion. Thus, the microorganism according to the embodiments of the present disclosure can be prepared into a pure bacterial fermentation broth, which can quickly and sufficiently precipitate starch, thereby improving starch production efficiency and having a good application prospect.

In yet another aspect of the present disclosure, the present disclosure provides uses of the aforementioned microorganism or fermentation broth in precipitating a starch emulsion. As mentioned above, the microorganism or fermentation broth according to the embodiments of the present disclosure has good flocculation rate and starch yield for the starch emulsion, and can quickly and sufficiently precipitate the starch, thereby improving starch production efficiency and having a good application prospect.

In another aspect of the present disclosure, the present disclosure provides a method for precipitating a starch emulsion. According to the embodiments of the present disclosure, the method includes the following steps: mixing the microorganism or the fermentation broth with a starch emulsion, and still standing. As mentioned above, the *Leuconostoc citreum* has good flocculation rate and starch yield, and thus the starch can be quickly and sufficiently precipitated by mixing it with a starch emulsion. Therefore, the method for precipitating a starch emulsion according to the embodiments of the present disclosure is simple in operation and has high efficiency and low cost, suitable for large-scale production.

According to the embodiments of the present disclosure, a concentration of the microorganism in the fermentation broth ranges from $1 \times 10^9$ CFU/ml to $5 \times 10^9$ CFU/mL, a starch concentration in the starch emulsion ranges from 10 g/L to 40 g/L, and a volume ratio of the fermentation broth to the starch emulsion is $1:(10^{-15})$. The above conditions are obtained by Applicant through a large number of experiments. By contacting a sufficient amount of *Leuconostoc citreum* with starch, the starch can be sufficiently precipitated, thereby further improving the starch yield.

Additional aspects and advantages of the present disclosure will be partially set forth as below, and they will be obvious from the following description or may be learned by practice of implementing the present disclosure.

BRIEF DESCRIPTION OF DRAWINGS

The above and/or additional aspects and advantages of the present disclosure will become apparent and easily understandable from the description of embodiments with reference to the following drawings, in which.

DESCRIPTION OF EMBODIMENTS

Solutions of the present disclosure will be explained with examples below. Those skilled in the art will understand that the following examples are only used to illustrate the present disclosure, and should not be regarded as limitations of the scope of the present disclosure. The specific technologies or conditions that are not indicated in the embodiments shall be those described in the literatures in the related field or according to the product manuals. The reagents or instruments without specifying the manufacturers are conventional products that are commercially available.

Example 1

I. Isolating and Purifying Lactobacilli 1. 10 ml of naturally fermented sour liquor of sweet potato was mixed with 90 ml of sterile physiological saline to prepare gradient diluted sample suspensions, with the gradient concentrations of $10^{-1}$, $10^{-2}$, $10^{-3}$, $10^{-4}$, $10^{-5}$ and $10^{-6}$.

2. Using a MRS medium as a selective medium, 200 μl of each gradient diluent was evenly coated on the MRS agar medium, and cultured at 37° C. for 48 h to obtain a single colony.

3. Plates corresponding to the gradient concentrations of $10^{-4}$, $10^{-5}$ and $10^{-6}$ were selected as screening objects, and for each plate, one single representative pure colony with a different shape was selected, and the obtained single colony was continuously purified twice by mean of zigzag streaking and three-zone streaking. 74 single colonies were purified in total, each of them was picked and put into a MRS broth, and cultured at 37° C. for 48 hours.

4. The purified bacteria solutions were numbered with SJ-1 to SJ-74; under aseptic conditions, the bacteria solution was mixed with sterilized glycerol with a concentration of 50% in a volume ratio of 1:1 in a frozen storage tube, and a final concentration of the glycerol was 25%, and the mixture was stored in a refrigerator at −80° C.

5. The MRS agar medium contained the following components: 10.0 g of peptone, 8.0 g of beef extract powder, 4.0 g of yeast extract powder, 20.0 g of glucose, 2.0 g of dipotassium hydrogen phosphate, 2.0 g of diammonium hydrogen citrate, 5.0 g of sodium acetate, 0.2 g of magnesium sulfate, 0.04 g of manganese sulfate, 14.0 g of agar, 1.0 g of tween 80, with a pH value of 6.5±0.2, and the volume was adjusted to 1 L with water.

6. The MRS broth culture medium contained the following components: 10.0 g of peptone, 8.0 g of beef extract powder, 4.0 g of yeast extract powder, 20.0 g of glucose, 2.0 g of dipotassium hydrogen phosphate, 2.0 g of diammonium hydrogen citrate, 5.0 g of sodium acetate, 0.2 g of magnesium sulfate, 0.04 g of manganese sulfate, 1.0 g of tween 80, with a pH value of 6.5±0.2, and the volume was adjusted to 1 L with water.

II. Screening Strains for High-Efficient Flocculating and Precipitating Starch

1. The strains with serial numbers of SJ-1 to SJ-74 were activated, rejuvenated, inoculated and expanded for culture. The specific operation was as follows: dipping the bacteria solution in a glycerol tube with a sterile inoculation ring, culturing it on a MRS agar medium by means of zigzag streaking and three-zone streaking at 37° C. for 48 h, and selecting and culturing a single colony in a MRS broth at 37° C. for 48 h, where the bacteria solution was the seed solution; adsorbing the seed culture solution and inoculating in a 10 ml MRS broth for expanded culture according to a volume ratio of 1%, so as to obtain a pure bacterial fermentation solution; culturing each strain to a stable stage, and controlling the concentration of the bacteria solution to be $1.2 \times 10^9$ CFU/ml.

2. Using flocculation rate and starch yield as screening indexes, 2 ml of pure bacteria solution was added into 25 ml of sweet potato starch emulsion (25 g/L), and then it was left to settle for 20 min; the flocculation rate and starch yield of the starch emulsion under the effect of each strain were calculated, and the strain with the highest activity in terms of starch flocculation and precipitation was screened.

3. The flocculation rate of the starch emulsion was determined as follows. two parts of 25 ml of starch emulsion (25 g/L) were prepared with distilled water and sweet potato starch, one of the two parts for control and the other for treatment. The bacteria solution was shaken evenly and divided into two parts; 2 ml of one part of the bacteria solution was added into the starch emulsion for treatment, shaken up down for 1 min and stood for 20 min; the supernatant was taken at a level of 1 cm below the liquid surface and the absorbance thereof was measured on a visible spectrophotometer, at a wavelength of 550 nm, which served as the treated sample and designated as $A_2$. The other part of bacteria solution was inactivated first, then centrifuged and discarded the supernatant to obtain the bacteria, and then added with the same volume of fresh MRS broth was prepared as a control bacteria solution; 2 ml of the control bacteria solution was added to the control starch emulsion; the remaining steps were the same as those for the treated sample, the measured absorbance was recorded as $A_1$.

The flocculation rate was calculated with the following equation:

$$FR = (A_1 - A_2)/A_1 \times 100\%,$$

where $A_1$ represents $OD_{550}$ of the control supernatant, and $A_2$ represents $OD_{550}$ of the treated supernatant.

4. The starch yield was determined as follows. 25 ml of starch emulsion (25 g/L) was prepared with distilled water and sweet potato starch, and 2 ml of a fermentation broth was added into the starch emulsion and shaken up and down for 1 min and then stood for 20 min for precipitation; then, the supernatant of the starch emulsion was discarded, the precipitated starch was placed into an oven and dried for 3 h to a constant weight, taken out and cooled to room temperature in a desiccator, weighed, and then placed back into the oven and dried for 0.5 h to a constant weight, cooled and weighed until the difference between the masses before and after the operation was smaller than 0.002 g. The calculation formula was as follows:

Starch yield=mass of precipitated starch (dry basis)/ mass of starch in starch emulsion (dry basis)× 100%     (5)

Figure 1:
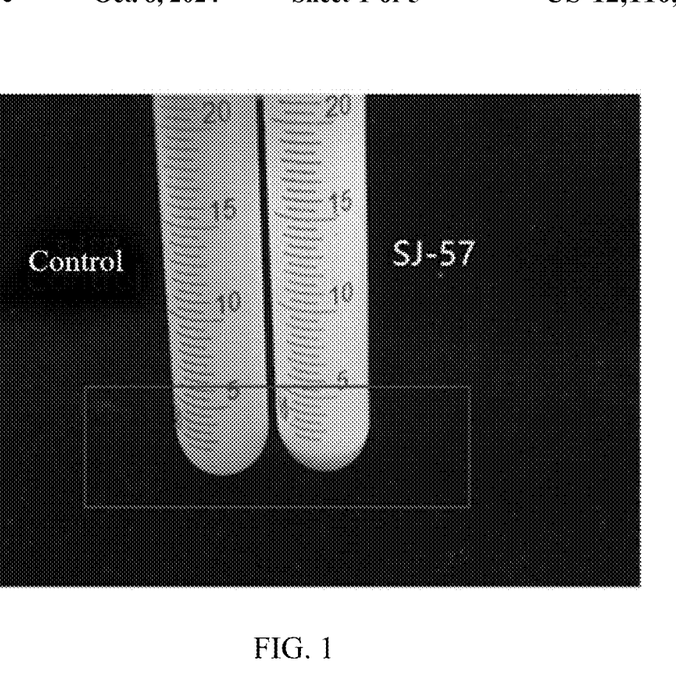
FIG. 1 schematically illustrates effect comparison of a control group and a treatment group at a time when precipitating a starch emulsion with *Leuconostoc citreum* according to an embodiment of the present disclosure for 1 min.
Figure 2:
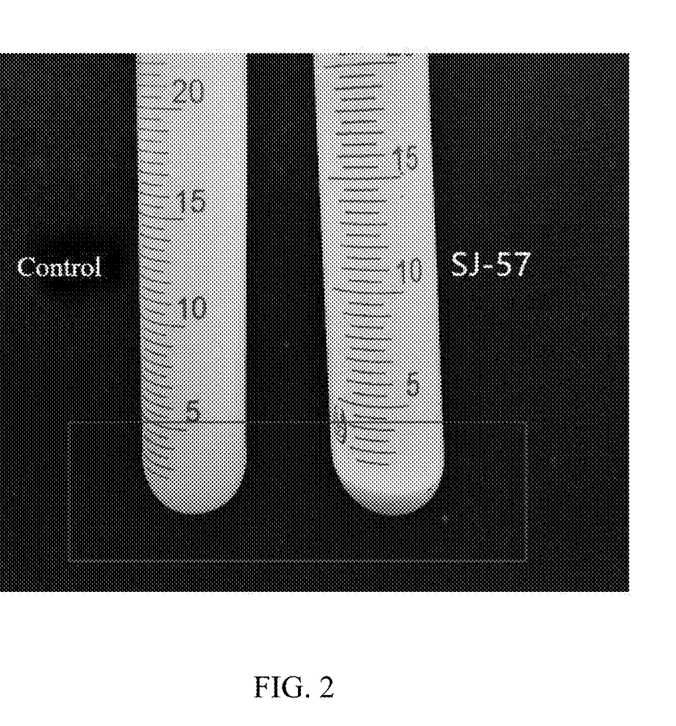
FIG. 2 schematically illustrates effect comparison of a control group and a treatment group at a time when precipitating a starch emulsion with *Leuconostoc citreum* according to an embodiment of the present disclosure for 3 min.
Figure 3:
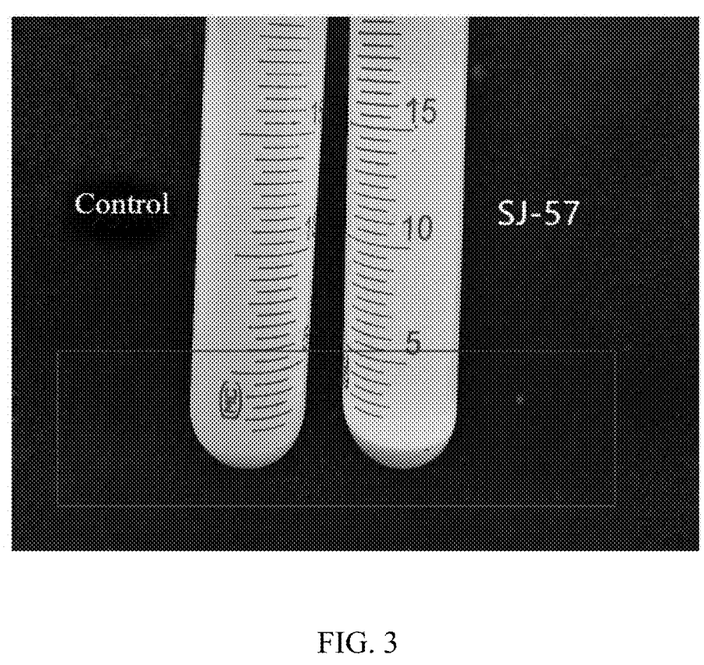
FIG. 3 schematically illustrates effect comparison of a control group and a treatment group at a time when precipitating a starch emulsion with *Leuconostoc citreum* according to an embodiment of the present disclosure for 15 min.

5. During the screening process, 7 strains were found to have flocculation and sedimentation effect on the starch emulsion. According to the results in Table 1, the SJ-57 bacteria solution has the highest flocculation rate and starch yield. FIG. 1 to FIG. 3 illustrate the situations of the starch emulsion added with the SJ-57 bacteria solution and the starch emulsion added with the control bacteria solution at times when precipitating for 1 min, 3 min, and 15 min, respectively. It can also be seen from the figures that starch precipitated at the bottom of the starch emulsion added with the SJ-57 bacteria solution is obviously more than that of the control sample.

TABLE 1

Flocculation rate and starch yield of 7 strains with high flocculation activity isolated from sweet potato acidic steeping liquor

| Strain No. | SJ-5 | SJ-14 | SJ-36 | SJ-45 | SJ-46 | SJ-48 | SJ-57 |
|---|---|---|---|---|---|---|---|
| Flocculation rate % | 15.18 ± 3.45 | 28.74 ± 5.69 | 27.36 ± 2.78 | 31.52 ± 9.98 | 47.78 ± 2.48 | 33.23 ± 0.06 | 55.56 ± 2.96 |
| Starch yield % | 71.45 ± 0.02 | 75.01 ± 1.13 | 74.42 ± 0.15 | 75.08 ± 0.77 | 80.07 ± 0.02 | 77.66 ± 0.66 | 84.57 ± 0.07 |

III. Identification of the SJ-57 Strain

1. The molecular identification of the SJ-57 was carried out by using the genomic DNA of the SJ-57 as a template to carry out PCR amplification with a universal primer 16S rRNA of bacterial gene. Specific sequencing was performed as follows.

(1) Extraction of bacterial genomic DNA: a bacterial genomic DNA extraction kit was used.

(2) PCR amplification: the universal primer 16S rRNA of bacterial gene was used: 27F: AGAGTTTGATCCTGGCTCAG (SEQ ID NO: 1); 1492R: GGCTACCTTGTTACGACTT (SEQ ID NO: 2). The reaction procedure was as below: pre-denaturation at 95° C. for 10 min, denaturation at 94° C. for 30 seconds, annealing at 55° C. for 30 seconds, extension at 72° C. for 1.5 min, repeated for 30 cycles; extension at 72° C. for 10 min and preserved at 4° C.

(3) Gel electrophoresis: 1% agarose electrophoresis was used, and the electrophoresis was observed after treating at 150 V and 100 mA for 20 min.

(4) Purification and recovery: the target band was cut, and the recovered product was sequenced.

2. BLAST search of 16S rRNA gene sequence was performed in the NCBI nucleic acid database, and compared with the existing sequences in the database in terms of homology. The results of sample sequencing and splicing were as follows:

```
                                                            (SEQ ID NO: 3)
ATCTGACTTAGACGGCTCCTCCCGAAGGTTAGGCCACCGGCTTTGGGCATTACAAACTCC        60

CATGGTGTGACGGGCGGTGTGTACAAGACCCGGGAACGTATTCACCGCGGCGTGCTGATC       120

CGCGATTACTAGCGATTCCGACTTCGTGCAGTCGAGTTGCAGACTGCAGTCCGAACTGAG       180

ACGTACTTTAAGAGATTAGCTCACCTTCGCAGGTTGGCAACTCGTTGTATACGCCATTGT       240

AGCACGTGTGTAGCCCAGGTCATAAGGGGCATGATGATCTGACGTCGTCCCCGCCTTCCT       300

CCGGTTTGTCACCGGCAGTCTCGCTAGAGTGCCCAACTGAATGCTGGCAACTAACAATAA       360

GGGTTGCGCTCGTTGCGGGACTTAACCCAACATCTCACGACACGAGCTGACGACGACCAT       420

GCACCACCTGTCACTTTGTCTCCGAAGAGAACACTTCTATCTCTAAAAGCTTCAAAGGAT       480

GTCAAGACCTGGTAAGGTTCTTCGCGTTGCTTCGAATTAAACCACATGCTCCACCGCTTG       540

TGCGGGTCCCCGTCAATTCCTTTGAGTTTCAACCTTGCGGTCGTACTCCCCAGGCGGAAT       600

ACTTAATGCGTTAGCTTCGGCACTAAGAGGCGGAAACCTCCTAACACCTAGTATTCATCG       660

TTTACGGTGTGGACTACCAGGGTATCTAATCCTGTTTGCTACCCACACTTTCGAGCCTCA       720
```

```
ACGTCAGTTGTTGTCCAGTAAGCCGCCTTCGCCACTGGTGTTCTTCCATATATCTACGCA    780

TTCCACCGCTACACATGGAGTTCCACTTACCTCTACAACACTCAAGTTAACCAGTTTCCA    840

ATGCCATTCCGGAGTTGAGCTCCGGGCTTTCACATCAGACTTAATCAACCGTCTGCGCTC    900

GCTTTACGCCCAATAAATCCGGATAACGCTCGGGACATACGTATTACCGCGGCTGCTGGC    960

ACGTATTTAGCCGTCCCTTTCTGGTATGGTACCGTCAAACTAAAATCATTCCCTATTTTA   1020

GCATTTCTTCCCATACAACAGTGCTTTACGACCCGAAAGCCTTCATCACACACGCGGCGT   1080

TGCTCCATCAGGCTTGCGCCCATTGTGGAAGATTCCCTACTGCAGCCTCCCGTAGGAGTT   1140

TGGGCCGTGTCTCAGTCCCAATGTGGCCGATCAGTCTCTCAACTCGGCTATGCATCATCG   1200

TCTTGGTAAGCCTTTACCCCACCAACTAACTAATGCACCGCGGATCCATCTCTAGGTGAC   1260

GCCGTAGCGCCTTTTAACTTGATATCATGCGATACTAAGTTTTATTCGGTATTAGCATCT   1320

GTTTCCAAATGTTATCCCCAGCCTTGAGGCAGGTTATCCACGTGTTACTCACCCGTTCGC   1380

CACTCGCTTGAAAGGTGCAAGCACCTCTCGCTGCGCGTCGACTGCATGTATAGCCCCCCC   1440

CC.                                                            1442
```

The results of homology analysis indicate that the sequence has high homology with each species of *Leuconostoc citreum* and the homology can be more than 99%.

At the same time, Applicant compared and analyzed the 16S rRNA gene sequences of other strains in Table 1, and identified SJ-5 as *Weissella confusa*, SJ-14 as *Leuconostoc mesenteroides*, and SJ-36 as *Leuconostoc mesenteroides*, SJ-45 as *Leuconostoc mesenteroides*, SJ-46 as *Leuconostoc holzapfelii*, and SJ-48 as *Leuconostoc mesenteroides*.

Figure 4:
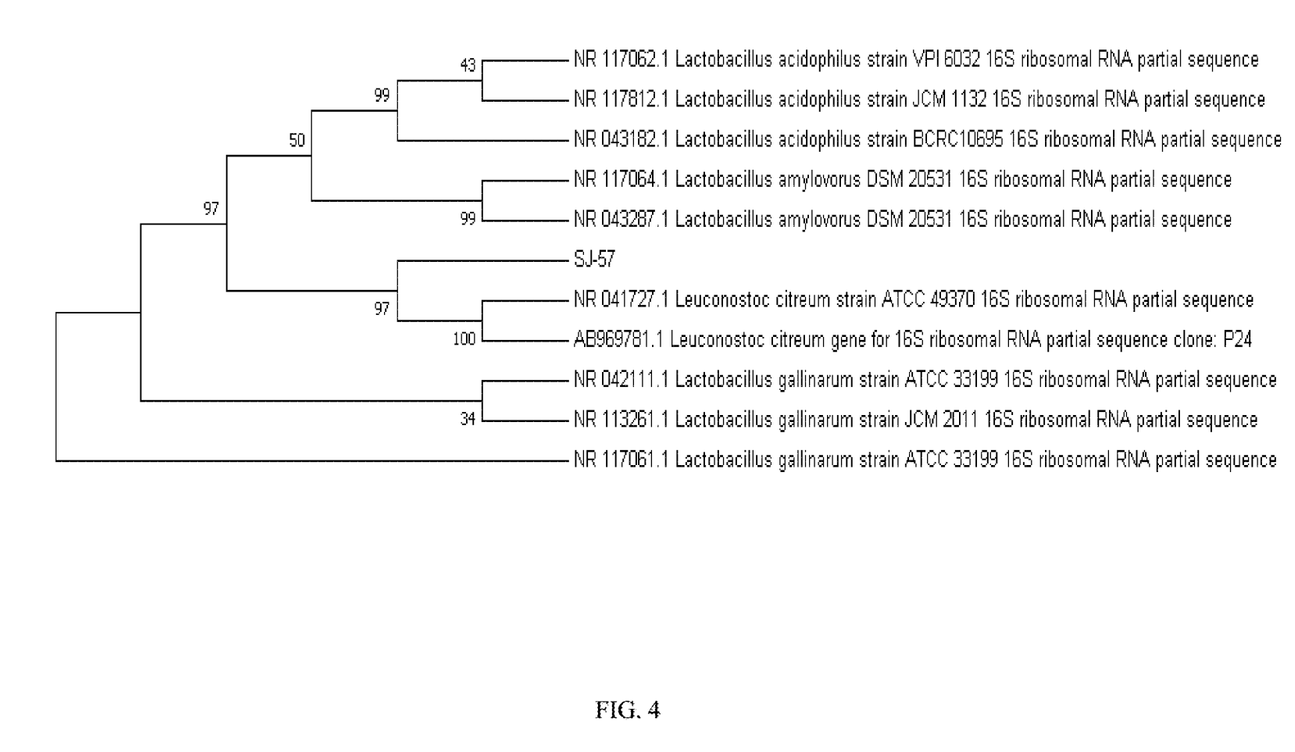
FIG. 4 illustrates a phylogenetic tree of gene sequence of SJ-57 strain according to an embodiment of the present disclosure.

3. 16S rRNA gene sequences of related strains were selected from GenBank, Clustal W multiple alignment was carried out by MEGA 7 software, phylogenetic tree was constructed by the Neighbour-joining method, and bootstrap analysis was carried out, with 1000 times of repetitions. The results are illustrated in FIG. 4. It can be seen from the phylogenetic tree that SJ-57 belongs to the same ethnic group as two strains of *Leuconostoc citreum*, with homology up to 97%.

Figure 5:
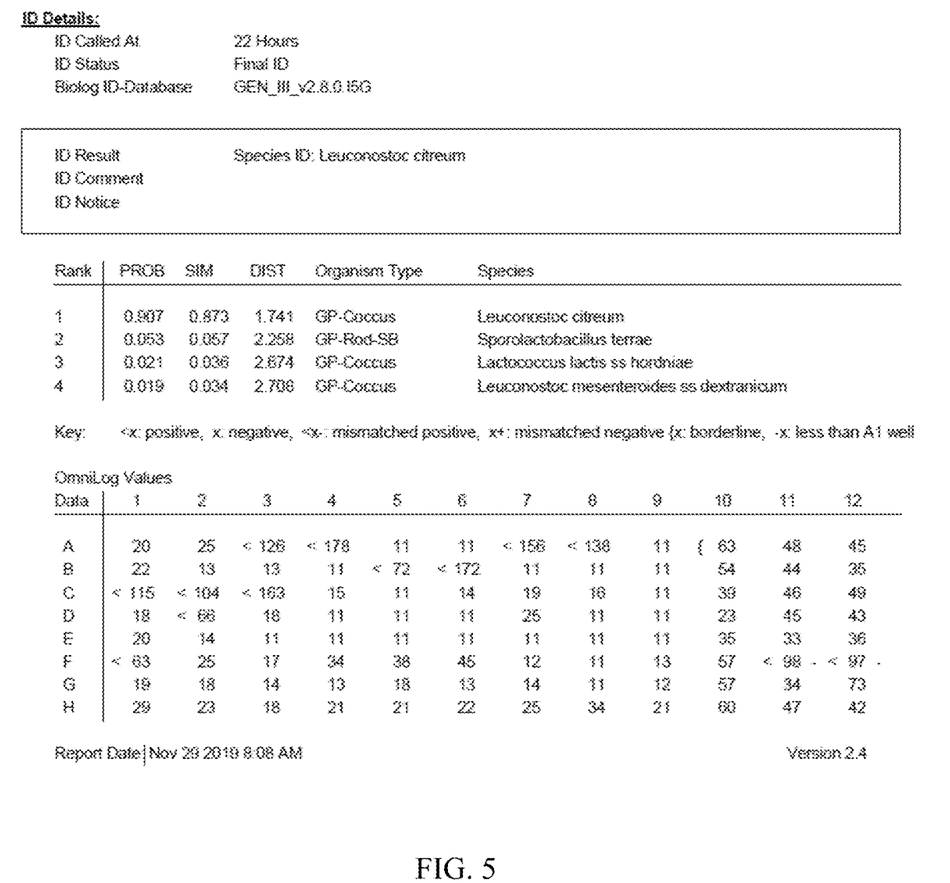
FIG. 5 illustrates a schematic diagram of an identification result analysis of BIOLOG automatic micro-analysis system according to an embodiment of the present disclosure.
Figure 6:
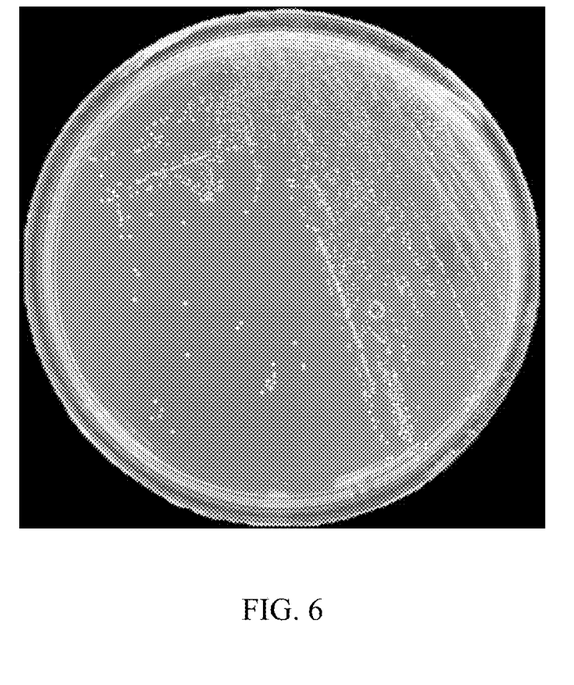
FIG. 6 illustrates a colony morphology of SJ-57 strain in a MRS agar medium according to an embodiment of the present disclosure.

4. The SJ-57 strain was identified by a BIOLOG automatic micro-analysis system. The results are illustrated in FIG. 5. Through the identification with such a system, the similarity between SJ-57 and *Leuconostoc citreum* can be 87.3%. According to the above identification results, the SJ-57 strain was finally identified as one strain of *Leuconostoc citreum*, named as *Leuconostoc citreum* WSJ-57. FIG. 6 illustrates a colony morphology of this strain in MRS agar medium.

In the present disclosure, the expressions "one embodiment", "some embodiments", "examples", "specific examples", "some examples", etc. mean that the specific features, structures, materials, or characteristics described in conjunction with the embodiment or example are included in at least one embodiment or example of the present disclosure. In this specification, the above terms do not necessarily refer to the same embodiment or example. Moreover, the specifically described features, structures, materials or characteristics can be combined in any one or more embodiments or examples in a suitable manner. In addition, those skilled in the art can combine the different embodiments or examples and the features of the different embodiments or examples described in this specification without contradicting each other.

Although the embodiments of the present disclosure have been shown and described above, it can be understood that the above-mentioned embodiments are exemplary and should not be construed as limitations of the present disclosure. Those skilled in the art can make changes, modifications, replacements and modifications to the above-mentioned embodiments without departing from the scope of the present disclosure.

What is claimed is:

1. A method for precipitating a starch emulsion, the method comprising:
   mixing (i) a fermentation broth containing a culture of *Leuconostoc citreum* WSJ-57, deposited under accession number CGMCC No. 19201, with (ii) a starch emulsion, to produce a mixture; and
   performing stand treatment of the mixture sufficient to precipitate the starch emulsion.

2. The method according to claim 1, wherein a concentration of the *Leuconostoc citreum* WSJ-57 in the fermentation broth ranges from $1\times10^9$ CFU/mL to $5\times10^9$ CFU/mL, a starch concentration of the starch emulsion ranges from 10 g/L to 40 g/L, and a volume ratio of the fermentation broth to the starch emulsion ranges from 1:10 to 1:15.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: universal primer 27F

<400> SEQUENCE: 1
agagtttgat cctggctcag                                             20

<210> SEQ ID NO 2
<211> LENGTH: 19
<212> TYPE: DNA
<213> ORGANISM: Artificial Sequence
```

<220> FEATURE:
<223> OTHER INFORMATION: universal primer 1492R

<400> SEQUENCE: 2
ggctaccttg ttacgactt                                               19

<210> SEQ ID NO 3
<211> LENGTH: 1442
<212> TYPE: DNA
<213> ORGANISM: Artificial Sequence
<220> FEATURE:
<223> OTHER INFORMATION: Synthesized Sequence

<400> SEQUENCE: 3
atctgactta gacggctcct cccgaaggtt aggccaccgg ctttgggcat tacaaactcc    60
catggtgtga cgggcggtgt gtacaagacc cgggaacgta ttcaccgcgg cgtgctgatc   120
cgcgattact agcgattccg acttcgtgca gtcgagttgc agactgcagt ccgaactgag   180
acgtacttta agagattagc tcaccttcgc aggttggcaa ctcgttgtat acgccattgt   240
agcacgtgtg tagcccaggt cataaggggc atgatgatct gacgtcgtcc ccgccttcct   300
ccggtttgtc accggcagtc tcgctagagt gcccaactga atgctggcaa ctaacaataa   360
gggttgcgct cgttgcggga cttaacccaa catctcacga cacgagctga cgacgaccat   420
gcaccacctg tcactttgtc tccgaagaga acacttctat ctctaaaagc ttcaaaggat   480
gtcaagacct ggtaaggttc ttcgcgttgc ttcgaattaa accacatgct ccaccgcttg   540
tgcgggtccc cgtcaattcc tttgagtttc aaccttgcgg tcgtactccc caggcggaat   600
acttaatgcg ttagcttcgg cactaagagg cggaaacctc ctaacaccta gtattcatcg   660
tttacggtgt ggactaccag ggtatctaat cctgtttgct acccacactt tcgagcctca   720
acgtcagttg ttgtccagta agccgccttc gccactggtg ttcttccata tatctacgca   780
ttccaccgct acacatggag ttccacttac ctctacaaca ctcaagttaa ccagtttcca   840
atgccattcc ggagttgagc tccgggcttt cacatcagac ttaatcaacc gtctgcgctc   900
gctttacgcc caataaatcc ggataacgct cgggacatac gtattaccgc ggctgctggc   960
acgtatttag ccgtcccttt ctggtatggt accgtcaaac taaaatcatt ccctatttta  1020
gcatttcttc ccatacaaca gtgctttacg acccgaaagc cttcatcaca cacgcggcgt  1080
tgctccatca ggcttgcgcc cattgtggaa gattccctac tgcagcctcc cgtaggagtt  1140
tgggccgtgt ctcagtccca atgtggccga tcagtctctc aactcggcta tgcatcatcg  1200
tcttggtaag cctttacccc accaactaac taatgcaccg cggatccatc tctaggtgac  1260
gccgtagcgc cttttaactt gatatcatgc gatactaagt tttattcggt attagcatct  1320
gtttccaaat gttatcccca gccttgaggc aggttatcca cgtgttactc acccgttcgc  1380
cactcgcttg aaaggtgcaa gcacctctcg ctgcgcgtcg actgcatgta tagccccccc  1440
cc                                                                1442